US006183978B1

(12) United States Patent
Bronstein et al.

(10) Patent No.: US 6,183,978 B1
(45) Date of Patent: Feb. 6, 2001

(54) LUCIFERASE ASSAY, COMPOSITIONS AND KITS FOR USE IN CONNECTION THEREWITH

(75) Inventors: Irena Bronstein, Newton; Corinne E. M. Olesen, Bedford; John C. Voyta, Sudbury; Yu-Xin Yan, Burlington, all of MA (US)

(73) Assignee: Tropix, Inc., Bedford, MA (US)

( * ) Notice: Under 35 U.S.C. 154(b), the term of this patent shall be extended for 0 days.

(21) Appl. No.: 09/148,782

(22) Filed: Sep. 4, 1998

(51) Int. Cl.$^7$ ............................ C12Q 1/66; C12O 1/48
(52) U.S. Cl. .................................................. 435/8
(58) Field of Search ........................... 435/8, 15, 188, 435/194, 975

(56) References Cited

U.S. PATENT DOCUMENTS

| 3,962,037 | * | 6/1976 | Mitchell | 435/188 |
| 5,283,179 | * | 2/1994 | Wood | 435/8 |
| 5,618,682 | * | 4/1997 | Scheirer | 435/8 |
| 5,648,232 | * | 7/1997 | Squirrell | 435/34 |
| 5,650,289 |   | 7/1997 | Wood | 435/8 |

OTHER PUBLICATIONS

Analytical Biochemistry, 158, pp. 1–5 (1986), Ugarova, et al., "Bioluminescent Assay of Creatine Kinase Activity Using Immobilized Firefly Extract".
Analytical Biochemistry, 46, pp. 489–501 (1972), Holmsen, et al., "Determination of ATP and ADP in Blood Platelets: A Modification of the Firefly Luciferase Assay for Plasma".
Biochemical and Biophysical Reseqrch Communications, vol. 84, No. 3, pp. 816–822 (1978), Momsen, "Firefly Luciferase Reacts with $P^1$, $P^5$–DI (Adenosine–5'–)Pentaphosphate and Adenosine–5'–Tetraphosphate".
Analytical Biochemistry, 220, pp. 410–414 (1994), Brovko, et al., "Bioluminescent Assay of Bacterial Intracellular AMP, ADP, and ATP with the use of a coimmobilized Three–Enzyme Reagent (Adenylate Kinase, Pyruvate Kinase, and Firefly Luciferase)".
Analytical Biochemistry, 69, pp. 187–206 (1975), Kimmich,e t al., "Assay of Picomole Amounts of ATP, ADP, and AMP Using the Luciferase Enzyme System".
Journal of Applied Biochemistry, 5, pp. 437–445 (1983), Olsson, et al., "Leakage of Adenylate Kinase from Stored Blood Cells".
Archives of Biochemistry and Biophysics, vol. 217, No. 2, pp. 674–681 (1982), Kricka, et al. "Effect of Solvents on the Catalytic Activity of Firefly Luciferase".
National Defense Research Institute, Department 4, pp. 611–619, Lundin, et al., "Continuous Monitoring of ATP–Converting Reactions by Purified Firefly Luciferase". (1976).
Biochem, Biophys, Acta., 170, pp. 208–210 (1968), Cole, et al., "Interference of Myokinase in the Determination of ATP by Luciferase Assay".

* cited by examiner

Primary Examiner—Ardin H. Marschel
Assistant Examiner—Marjorie A. Moran
(74) Attorney, Agent, or Firm—Piper, Marbury Rudnick & Wolfe, LLP; Steven B. Kelber

(57) ABSTRACT

An assay for the presence of luciferase in a biological sample offers heightened sensitivity, signal intensity and persistence. The assay is sensitive down to 50 fg luciferase. The biological sample is combined with essential ingredients luciferin, ADP, myokinase and $Mg^{++}$. The myokinase converts ADP to ATP, necessary for the luciferase reaction, and AMP, which retards the reaction kinetics. The resulting assay exhibits a persistent glow emission which makes it adaptable to automation.

10 Claims, 5 Drawing Sheets

LUCIFERASE ASSAY, COMPOSITIONS AND KITS FOR USE IN CONNECTION THEREWITH

BACKGROUND OF THE INVENTION

1. Field of the Invention

This invention pertains to an assay format for the detection of the presence of luciferase, as a reporting molecule or target molecule, in an assay. The assay finds particular value in assays for the detection of luciferase present in a biological sample as the expression product of a luciferase gene transfected into a host cell as a reporter gene. Additionally, compositions useful in the assay method, and kits for performing the assay, are addressed.

2. Background of Prior Art

Chemiluminescent assays using luciferase as an enzyme to indicate the presence of ATP in a biological system or sample are widely described in the literature. Luciferase catalyzes chemiluminescent light release according to the following reaction system:

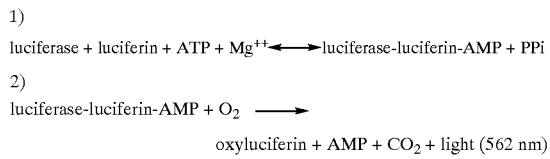

Although a variety of luciferase enzymes have been identified, and all that catalyze a similar reaction utilizing ATP may be used in conjunction with the invention of this application, the best characterized luciferase is firefly luciferase, the enzyme responsible for the characteristic "flash" of this particular beetle (*P. pyralis*). This luciferase is a 61–62 kD monomeric enzyme which catalyzes the light emission described above with a quantum yield of 0.88. The light naturally emitted at pH 7.8 is a green-yellow light (about 562 nm).

Luciferase assays for the quantitiation of luciferase enzyme are described in U.S. Pat. Nos. 5,652,289 and 5,283,179, Wood. A well known difficulty encountered in developing luciferase assays is the enzyme kinetics which produces a very rapid peak intensity, i.e., the "flash of light", coupled with a rapid decay to a very low level, is discussed extensively in these patents. The patents also address prior art attempts to solve this problem, including the addition of coenzyme A (CoA) and/or a sulfhydryl compound such as dithiothreitol (DTT) to support greater overall light release.

A wide variety of literature has been developed concerning luciferase assays, and methods to increase both peak light intensity and total light emission. Among the various alternatives explored is the selection of specific solvents, Kricka, et al., Arch. Biochemistry and Biophysics 217, 674–681 (1982), other SH compounds such as N-acetylcystein, Lundin, Bioluminescence and Chemiluminescence, and the addition of sodium arsenate and other salts, DeLuca et al., Analytical Biochemistry 95, 194–198 (1978).

Specific assays employing these formulations to detect target molecules at as low as picomolar concentrations are described in Olsson, et al., Journal of Applied Biochemistry 5, 437–445 (1983), Kimmich, et al., Analytical Biochemistry 69, 187–206 (1975), Brovko, et al., Analytical Biochemistry 220, 410–414 (1994), Momsen, Biochemical and Biophysical Research Communications 84, 816–822 (1978) and Holmsen, et al., Analytical Biochemistry 46, 489–501 (1972). Many of these references describe the role of myokinase, also known as adenylate kinase, for measurement of an adenine nucleotide with a luciferase reaction, (see, in particular, Brovko, Momsen, Olsen and Holmsen, supra). Myokinase is a ubiquitous enzyme found in both prokaryotic and eukaryotic cells, with a molecular weight in its monomeric form of about 21 kDa. An important feature of myokinase is its high substrate specificity to adenine nucleotides, being reactive with ADP, AMP and ATP. Myokinase catalyzes a bidirectional reaction:

Just as ATP and $Mg^{++}$ are essential components to drive the luciferase chemiluminescent reaction forward, AMP is a known inhibitor of the luciferase light-yielding reaction.

U.S. Pat. No. 5,618,682, Scheirer, addresses a luciferase assay based on the luciferase-luciferin reaction which is described as providing light emission over a period of up to 8 hours. In this assay, a sample, which is suspected of containing luciferase, is combined with the luciferase substrate luciferin, ATP, AMP, and other co-factors for promoting catalytic activity. Essential to this patent is the combination of both ATP, to support the luciferase-catalyzed reaction, and AMP, to retard the enzyme kinetics, so as to produce a sustained light emission.

As mentioned by Scheirer, luciferase has become important as a reporter molecule outside of the traditional environment of measurement of ATP, as an indicator of ATP synthesis, metabolism, or as an indicator for the presence of bacterial cells. A number of genes for luciferase have been identified and been demonstrated to be effective, when transfected, in expression in heterologous hosts. Thus, the luciferase gene has become an important reporter gene, since detection of the presence of luciferase in a recombinant cell candidate can be used in a wide variety of environments, provided light emission intensity and duration can be supported so as to enable for facile detection, and importantly, automated detection.

Accordingly, it remains an object of those of ordinary skill in the art to develop a luciferase assay which provides, simultaneously, sufficient sensitivity and light intensity, over a sustained period of time, to permit automated chemiluminescent detection of the presence of luciferase in a sample, particularly as a reporter gene in recombinant cell assays.

SUMMARY OF THE INVENTION

The above objects, and other objects developed more completely below, are met by an assay for the presence of luciferase which both increases the signal intensity of luciferase detection over existing methods, and provides for prolonged light emission, such that enhanced automated detection can be achieved. In contrast to prior art formulations employing AMP to inhibit light signal decay, and an initial ATP charge to promote the luciferase reaction, the inventive assay employs, in addition to luciferin, ADP and myokinase. The assay composition also includes magnesium, an essential component for the luciferase and myokinase reactions, and advantageously employs dithiothreitol (DTT) or other sulfhydryl compound or mixture of compounds to enhance the stability of the luciferase that may be present in the sample.

A first buffer (Buffer A) includes as an essential ingredient myokinase. Optional ingredients that may provide a greater signal intensity include magnesium and a sulfhydryl reducing compound such as DTT or β-mercaptoethanol. This buffer also comprises conventional buffering agents, such as N-[tris(hydroxymethyl)methyl]glycine (tricine) or other zwitteronic buffers, EDTA, other surfactants such as Triton X-100, and may comprise support materials such as glycerol.

In conducting the assay, two reaction buffers are prepared, the second comprising ADP and D-luciferin as essential components. This reaction buffer may be further comprised of conventional stabilizing components that do not affect the luciferase reaction, such as dextran.

Buffer A, comprising myokinase and optionally magnesium as essential ingredients, preferably in the form of $MgSO_4$, is added to a reaction vessel comprising the biological sample to be tested, typically cells in culture medium, although cell lysis preparations are also conventionally used. Thereafter, buffer B is added to the reaction vessel, and the vessel is incubated at ambient conditions for a brief period of time, about 10 minutes. Thereafter, the vessel is placed in a luminescence measuring device, such as a luminometer or other light detection device to determine light intensity. In an alternative embodiment, the two reaction buffers may be combined or "premixed" for a short period of time, and then added to the biological sample.

DESCRIPTION OF THE DRAWINGS

FIG. 1, the inventive assay is compared against a commercially available assay, LucLite™. S/N values are given for the assay, over a range of enzyme concentrations.

FIG. 2 demonstrates the kinetics and signal intensity achieved with the reaction, performed on transfected Hela cells, compared to a commercially available assay.

FIG. 3, using a fixed luciferase concentration, the effect, in terms of relative light units, of varying amounts of addition of myokinase (in buffer A) are graphically represented.

FIG. 4 presents a similar graphic representation, showing the effect of varying concentrations of $MgSO_4$ (in buffer A) over time. It should be noted that the culture medium present in assay contributes additional $Mg^{++}$.

In FIG. 5, the effect of premixing the two buffers, prior to combination with cell culture (transfected SK-NSH cells bearing the luciferase gene) is given.

DETAILED DESCRIPTION OF THE INVENTION

Figure 1:
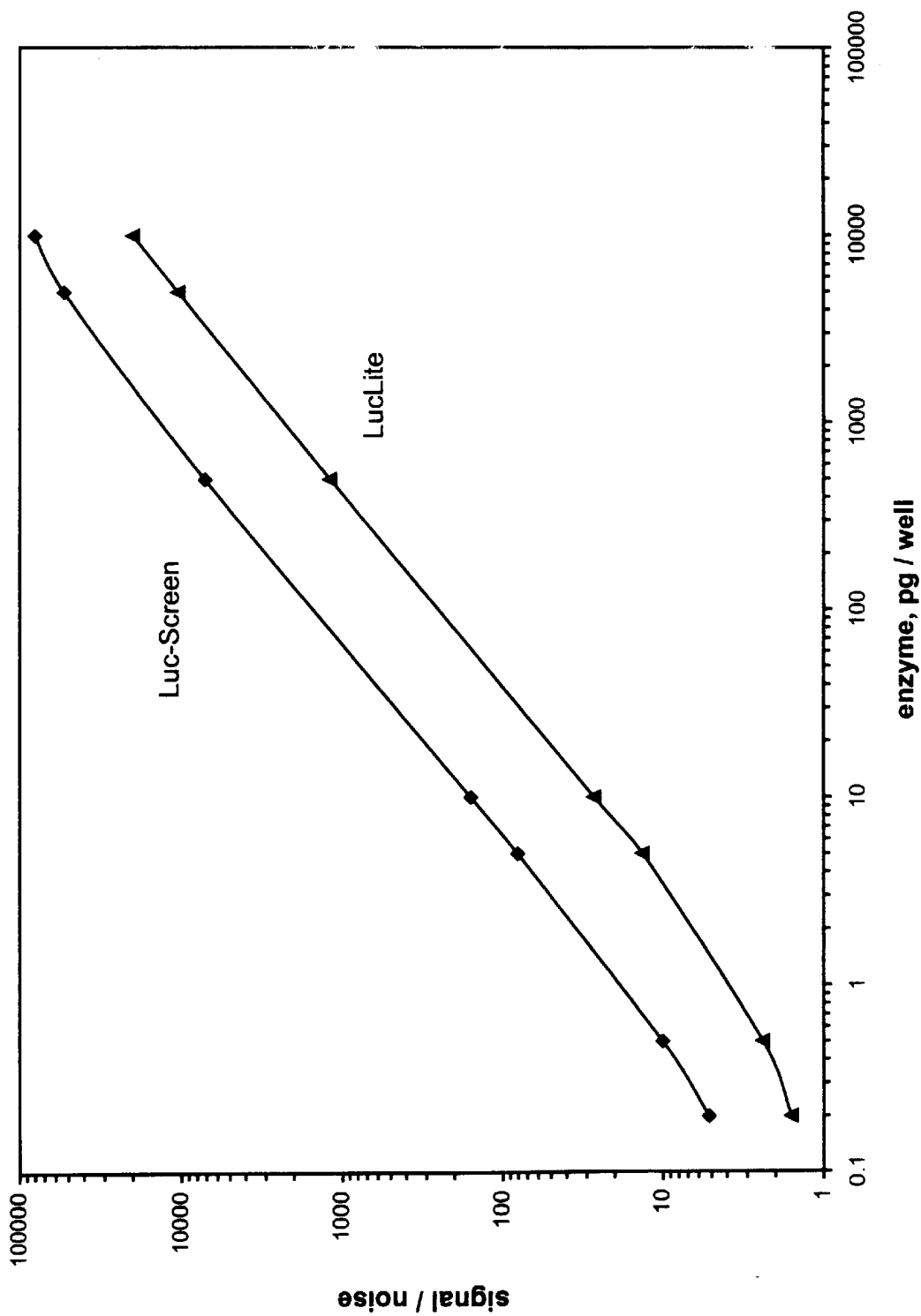
FIGS. 1–5 demonstrate the chemiluminescent performance of the inventive assay.
Figure 2:
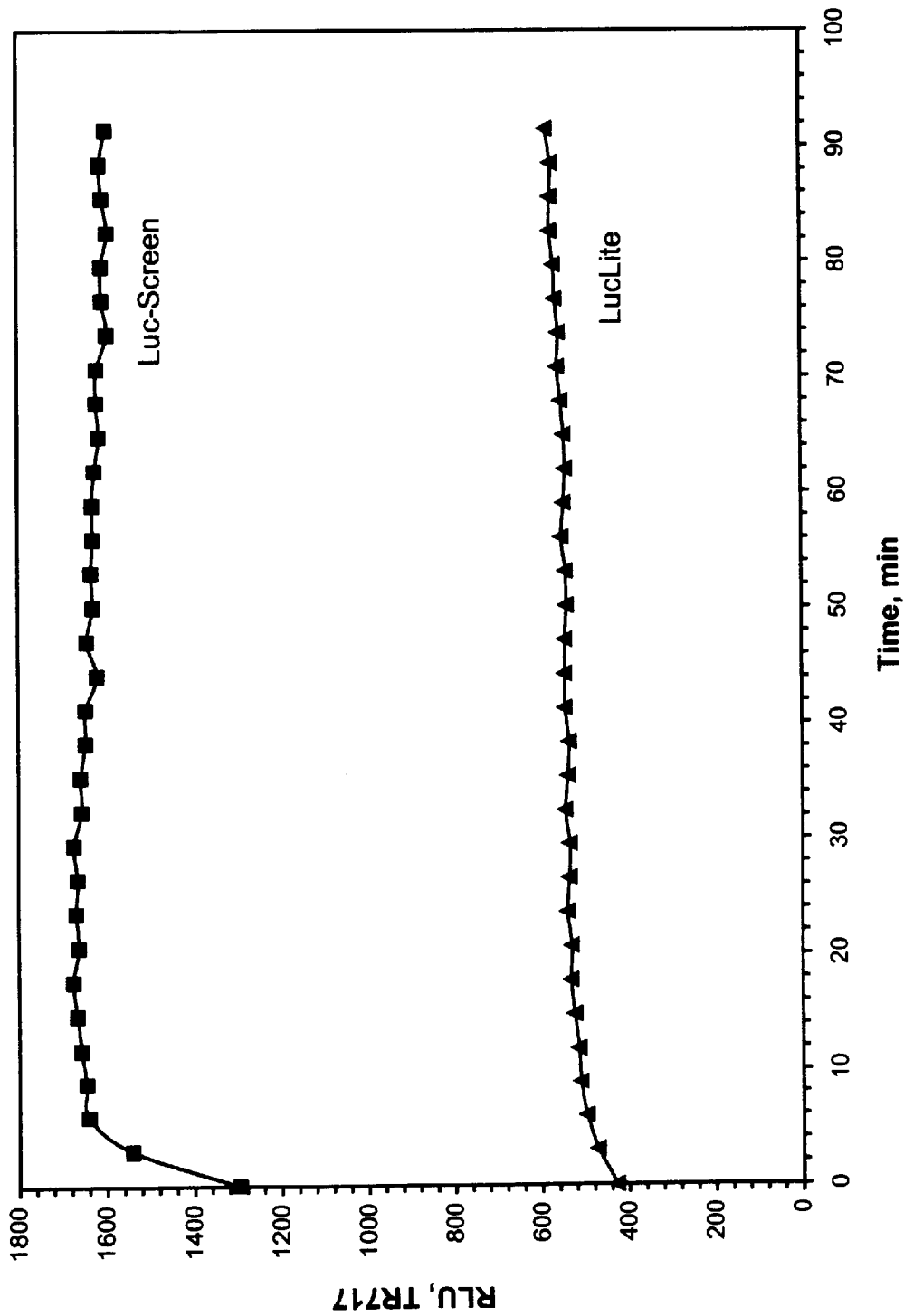
Figure 3:
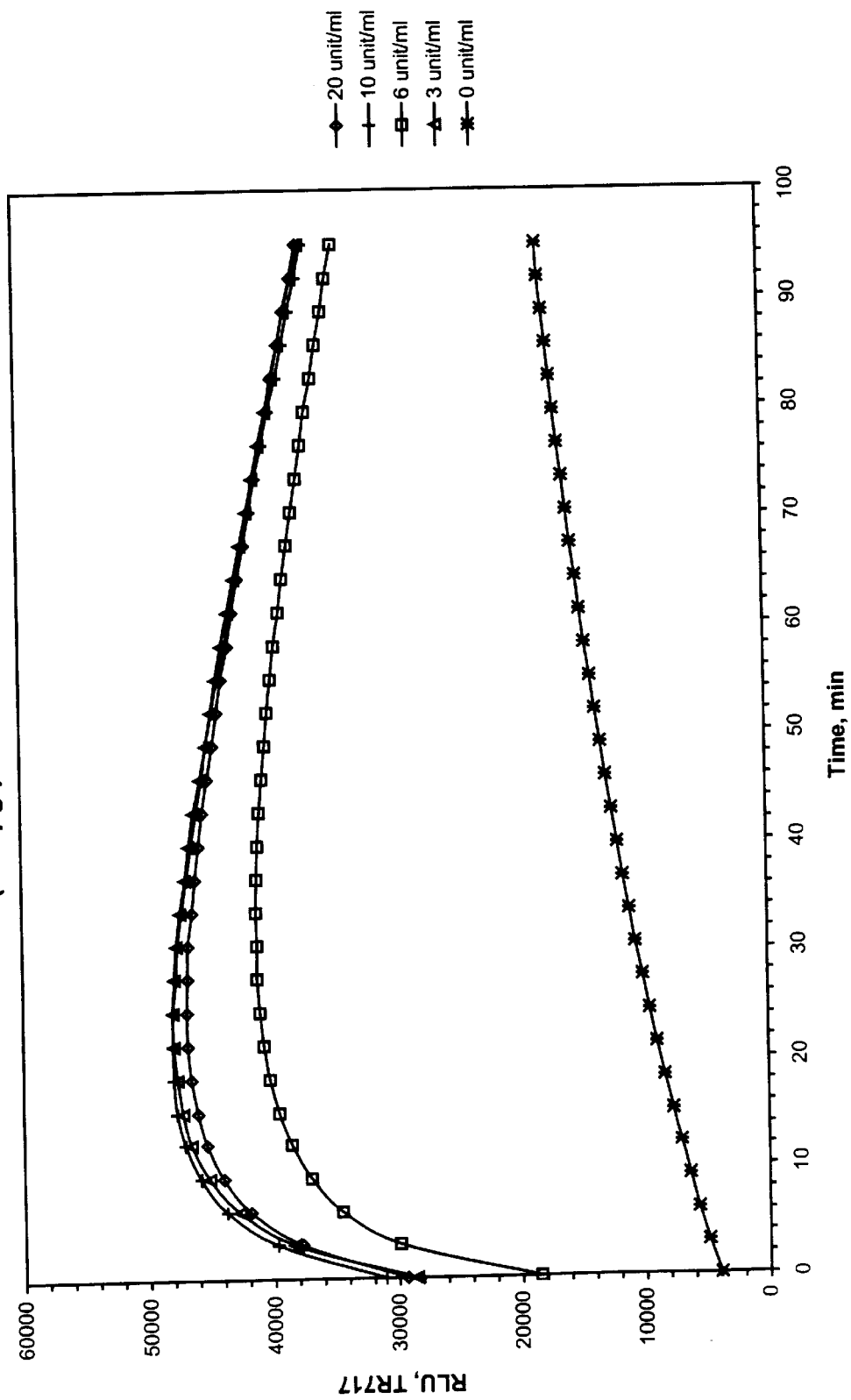
Figure 4:
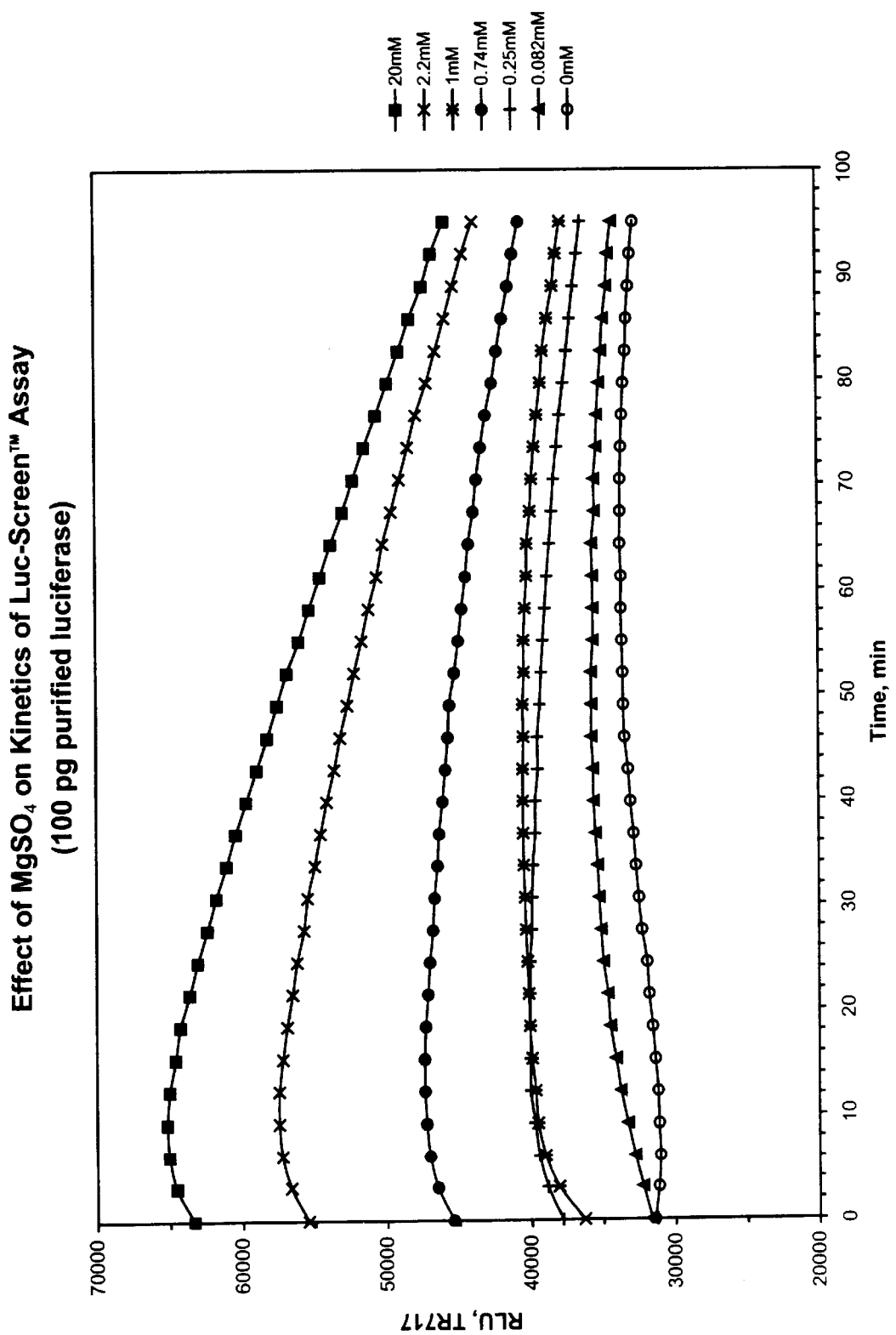

The luciferase assay of this invention, based on the addition of myokinase together with ADP, has been demonstrated to offer an increase in emission intensity, and sustained emission, in contrast to prior art available assays. A widely used luciferase assay is available under the mark LucLite. The assay of this invention, referred to as Luc-Screen™ is compared with this commercially available luciferase assay in FIG. 1. As clearly reflected in FIG. 1, wherein the signal/noise values for the two assays, over a wide range of enzyme concentrations are provided, the claimed invention exhibits improved performance. This assay was conducted according to the procedure described below, and generates an increase in sensitivity. As shown in FIG. 2, this assay exhibits an approximately 5-fold increase in signal intensity compared to a commercially available assay. The increased signal intensity provides improved assay performance that permits its use with samples containing the common culture media additive, phenol red.

Simultaneously, the sustained glow, as opposed to the flash encountered in the prior art, persists over an extended period, convenient for automation of the assay and high throughput of inspection, typically achieved using microtiter plates, which may include 96, 384 or more wells. Thus, the assay provides high signal intensity, with great sensitivity. In assays of this type, the inventive luciferase assay (referred to as Luc-Screen™) enables detection of as low as 50 femtograms of luciferase enzyme.

The assay calls for the use of two reaction buffers. Reaction buffer B employs ADP and D-luciferin as essential ingredients. ADP is the ultimate source of both a reactant, ATP, and the retardant, AMP. ADP concentration ranges from 0.2 $\mu$M–50 mM preferably 2 $\mu$M–10 mM, and is used in examples at 5 mM. D-luciferin is present in smaller amounts, 0.2 $\mu$M–2 mM, preferably 2 $\mu$M–1 mM, and as an example, 0.5 mM. This buffer can, but does not necessarily, incorporate buffer composition materials such as dextran. If incorporated, these are included in amounts of 0–10 mg/ml, preferably 1–5 mg/ml and 2 mg/ml by way of example.

Buffer A, includes as an essential component myokinase and may include tricine or a similar buffering agent well known to those skilled in the art. The reaction buffer comprises from 0.01–50 unit/ml myokinase.

Magnesium, present as $MgSO_4$ can be present in amounts of 0–100 mM, preferably in a range of 0.08–20 mM. An exemplary value is, as $MgSO_4$, 1 mM.

Advantageously, reducing compounds, include DTT, β-mercaptoethanol or other art-recognized sulfhydryl compounds may be present to stabilize luciferase present. The SH luciferase stabilizer can be present over a wide range from 0–100 mM, preferably 5–75 mM, and as an example 60 mM. Additional components such as, EDTA and Triton X-100 can also be present. Glycerol is also optionally present, over a wide range 0–20%. The exemplary reaction buffer is set forth below.

| # | Component | Concentration in the Buffer | Buffer |
|---|---|---|---|
| | Luc-Screen ™ Assay Reaction Buffer Composition | | |
| 1 | Myokinase | 6 unit/ml | A |
| 2 | Tricine | 10 mM | A |
| 3 | EDTA | 1 mM | A |
| 4 | DTT | 60 mM | A |
| 5 | $MgSO_4$ | 1 mM | A |
| 6 | Triton X-100 | 0.2% (v/v) | A |
| 7 | Glycerol | 10% (v/v) | A |
| 8 | ADP | 5 mM | B |
| 9 | D-luciferin | 0.5 mM | B |
| 10 | Dextran | 2 mg/ml | B |

It should be noted that many cell culture media preparations comprise phenol red as a pH indicator or monitor. The presence of phenol red typically produces a 2–4-fold decrease in signal intensity when the culture medium contains phenol red.

The signal of this reaction is typically read using a luminometer or similar light-sensitive instrument, although other conventional instruments can be used. To maintain steady light emission, the temperature during the assay and measurement phase should be maintained at about 25–27° C.

As described above, the assay is designed to detect the presence of luciferase in cells in the presence of culture medium. If necessary or desired, however, PBS, containing 0.5–2 mM $Mg^{++}$ and 1 mM $Ca^{++}$ can be substituted for the culture medium.

A standard test protocol is set forth below.

Luc-Screen™ Assay

Test Protocol

1. Allow Reaction Buffers A and B to warm to room temperature.
2. Add 50 µl of Buffer A to each well containing cells in 100 µl of culture medium with or without phenol red.
3. Add 50 µl of Buffer B to each well.
   (Timing between additions of Buffer A and Buffer B is not critical to assay performance.)
4. Incubate microplate at room temperature for 10 min.
5. Place microplate in a luminometer and measure signal intensity.

Figure 5:
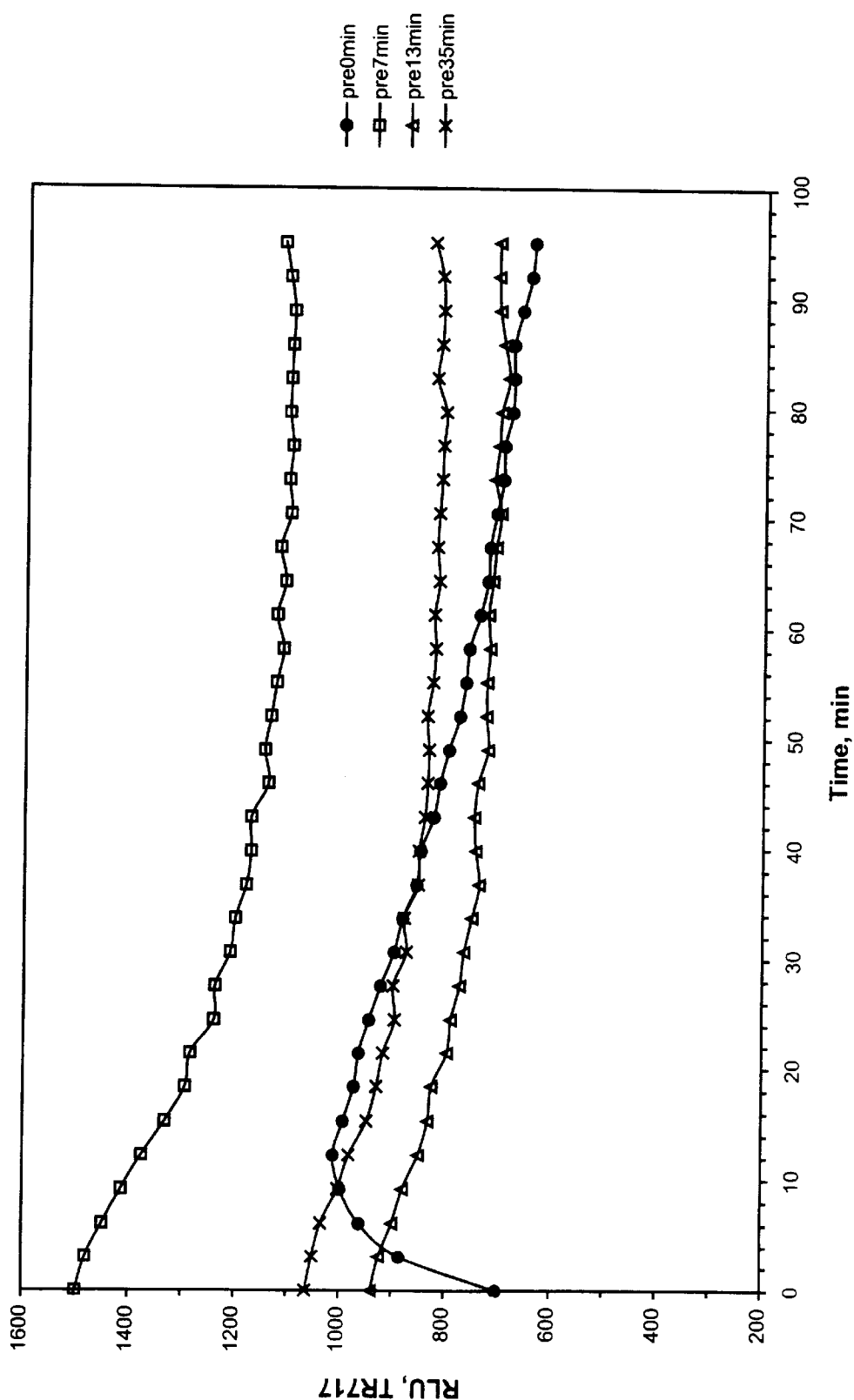

The effectiveness of this assay in detecting luciferase is reflected in FIG. 5. The above protocol is employed in detecting luciferase, by light emission, with SK-NSH cells, transfected with the gene for *P. pyralis* luciferase. Even in the presence of phenol red, the signal intensity is quite strong, and prolonged light emission enables automation. FIG. 5 illustrates the effects of "premixing", that is combining the two buffers, prior to adding them to the cell culture medium. As shown, premixing moderately improves signal intensity, but has no overall substantial impact on assay performance.

The assay described herein is highly sensitive, generates a strong, sustained signal, and is adaptable to automation. The system is more sensitive with higher light signal intensity than the leading commercial system, and is relatively insensitive to non-automated variations, such as concentration, timing of steps and the like.

The invention has been described above both generically, and with reference to specific embodiments. The specific embodiments are not intended to be limiting, and variations, particularly in terms of non-critical reaction buffer contents, concentrations, timing, temperature and the like will occur to those of ordinary skill in the art, without the exercise of inventive faculty. These variations remain within the scope of the invention, unless specifically excluded by the claim recitations set forth below.

What is claimed is:

1. A method of assaying for the presence of luciferase in a biological sample, comprising:
   combining said sample with a reaction composition which comprises luciferin, adenosine diphosphate (ADP) and myokinase;
   allowing said reaction composition to incubate with said biological sample; and
   inspecting said incubated biological sample and reaction composition to determine if light is emitted, wherein said light emission is indicative of the presence of luciferase in said biological sample and wherein the intensity of said light emission is a sustained glow that persists over an prolonged period of time to permit automated detection of the presence of luciferase in said sample.

2. The method of claim 1, wherein said reaction composition further comprises a sulfhydryl luciferase stabilizing agent.

3. The method of claim 1, wherein said reaction composition further comprises a source of $Mg^{++}$ ions.

4. The method of claim 2, wherein said reaction composition further comprises a source of $Mg^{++}$ ions.

5. The method of claim 1, wherein said reaction composition further comprises at least one buffering agent.

6. The method of claim 1, wherein said reaction composition further comprises at least one of dextran and glycerol.

7. The method of claim 1, wherein said reaction composition is formed by combining two reaction buffers, wherein said first buffer comprises myokinase, and said second buffer comprises ADP and luciferin and said first and second reaction buffer are combined to form said reaction composition.

8. The method of claim 7, wherein said first reaction buffer further comprises a source of $Mg^{++}$ ions, and a sulfhydryl (SH) luciferase stabilizing reducing compound.

9. The method of claim 8, wherein said SH compound is dithiothreitol, β-mercaptoethanol or mixtures thereof.

10. The method of claim 7, wherein said first reaction buffer further comprises a zwitterionic buffering agent and glycerol, and said second reaction buffer comprises dextran.

* * * * *